(12) United States Patent
Zemlak

(10) Patent No.: US 9,480,604 B2
(45) Date of Patent: Nov. 1, 2016

(54) EYE PROTECTION EMPLOYING LUMINESCENT MATERIALS FOR IONIZING RADIATION WARNINGS TO THE WEARER

(71) Applicant: Mason Zemlak, Grasswood (CA)

(72) Inventor: Mason Zemlak, Grasswood (CA)

(*) Notice: Subject to any disclaimer, the term of this patent is extended or adjusted under 35 U.S.C. 154(b) by 858 days.

(21) Appl. No.: 13/951,829

(22) Filed: Jul. 26, 2013

(65) Prior Publication Data

US 2014/0041105 A1 Feb. 13, 2014

Related U.S. Application Data

(60) Provisional application No. 61/680,565, filed on Aug. 7, 2012.

(51) Int. Cl.
*G01T 1/17* (2006.01)
*A61F 9/02* (2006.01)
*G01T 1/02* (2006.01)
*A61B 6/10* (2006.01)

(52) U.S. Cl.
CPC ............... *A61F 9/029* (2013.01); *G01T 1/023* (2013.01); *A61B 6/107* (2013.01)

(58) Field of Classification Search
CPC ........................................................ G01T 1/17
See application file for complete search history.

(56) References Cited

U.S. PATENT DOCUMENTS

| | | | |
|---|---|---|---|
| 3,597,054 A * | 8/1971 | Winter | 351/48 |
| 5,045,700 A | 9/1991 | Crowson | |
| 5,172,256 A * | 12/1992 | Sethofer et al. | 349/14 |
| 5,992,996 A | 11/1999 | Sawyer | |
| 2011/0116076 A1 * | 5/2011 | Chantry et al. | 356/51 |
| 2014/0256865 A1 * | 9/2014 | Boulton et al. | 524/406 |

* cited by examiner

*Primary Examiner* — David Porta
*Assistant Examiner* — Hugh H Maupin
(74) *Attorney, Agent, or Firm* — Kyle R. Satterthwaite; Ryan W. Dupuis; Ade & Company Inc.

(57) ABSTRACT

A protective eyewear device features a frame for supporting the protective eyewear on a user's head in a position placing one or more transparent or translucent viewing lenses of the eyewear device in front of the user's eyes, and one or more deposits of a radiation-reactive material located at or adjacent the one or more lenses and responsive to ionizing radiation exposure to produce a visual indication of said exposure to the user within a normally used field of vision of said user.

9 Claims, 2 Drawing Sheets

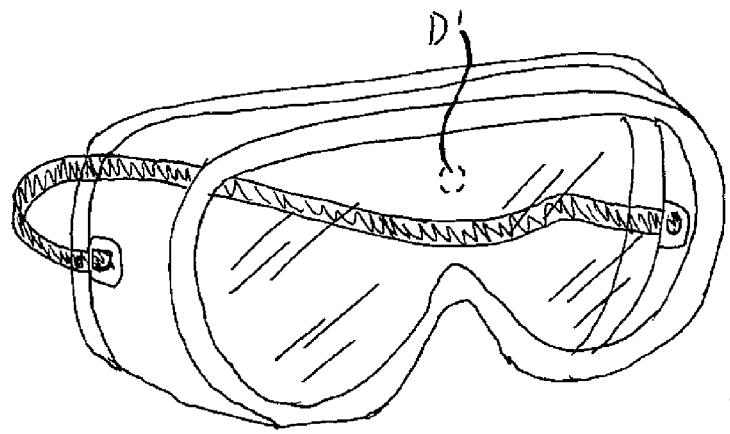
FIG. 2A
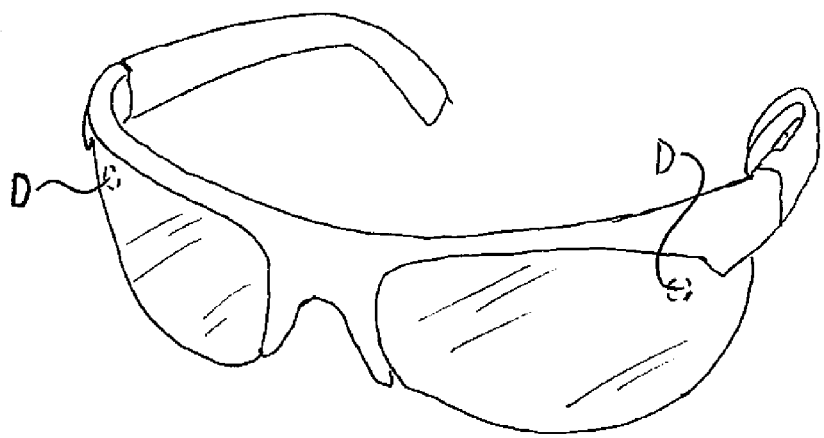
FIG. 2B
FIG. 2C
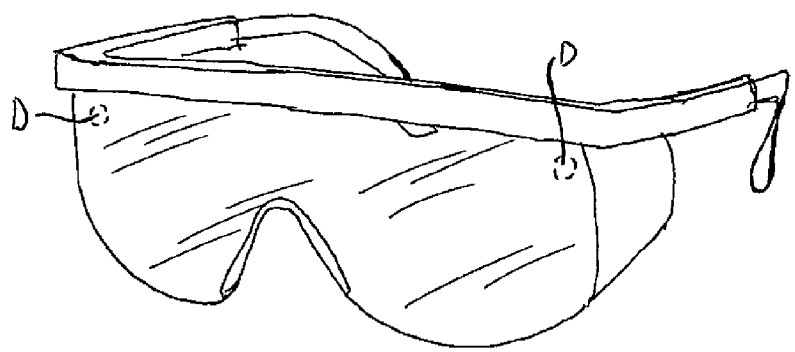

EYE PROTECTION EMPLOYING LUMINESCENT MATERIALS FOR IONIZING RADIATION WARNINGS TO THE WEARER

CROSS REFERENCE TO RELATED APPLICATIONS

This application claims benefit under 35 U.S.C. 119(e) of Provisional Application Ser. No. 61/680,656, filed Aug. 7, 2012.

FIELD OF THE INVENTION

The present invention relates generally to eye protection devices that provide the wearer with visible warning signals responsive to exposure to ionizing radiation, and particularly to eye protection device having luminescent materials present in the wearer's field of vision to provide visible signals indicative of ionizing radiation exposure.

BACKGROUND OF THE INVENTION

Safety is one of the fastest growing fields in Canada and the world. The market for new safety products and implemented procedures is growing at a phenomenal rate. The broadly accepted ideology in the construction, mining and maintenance sectors is that any new level of protection for workers and companies in general is welcomed with open arms.

The Canadian Nuclear safety commission regulates the safety equipment that is worn by nuclear energy workers. Industrial Radiographers use isotopes that give off Gamma radiation as well as use x-ray machines in order to radiograph materials and objects. They are required by law to wear 3 objects that record/warn the person of what radiation dose and quantity they are being exposed to. These three items are:

1) TLD (Thermo-Luminescent dosimeter) also known as a film badge. This is a small device that accurately measures the person's total absorbed dose. These are sent into Health Canada every two weeks by law for every nuclear energy worker to monitor short term and lifetime dose.
2) PAD (personal Alarming Dosimeter) This device gives a reading of the actual dose-rate (real-time) as well as gives off and audible warning that changes frequency with the dose-rate.
3) DRD (Direct Read Dosimeter) This is a device that records absorbed dose to a certain limit, can be read then reset to zero in the field.

It has been proposed in previous patents to incorporate radiation detection into safety glasses worn by the nuclear energy worker.

For example, U.S. Pat. No. 5,992,996 teaches a set of protective eyewear incorporating a chip holder supported on the eyewear frame and configured to receive a theremoluminescent dosimetry chip, which can be removed and read after a period of time in order to measure facial exposure to radiation.

U.S. Pat. No. 5,045,700 also incorporates a radiation detection solution into a pair of eyeglasses, but instead of a theremoluminescent dosimetry chip that requires regular monitoring and provides no instantaneous feedback on radiation exposure levels, a Geiger-Muller tube is used to detect radiation and trigger electronic lights to provide real-time visual feedback on radiation levels, including warning signals when dangerous radiation levels are detected. However, the system requires a significant number of electrical components in order to operate.

Other patents relating to radiation detection on a pair of eyeglasses include U.S. Pat. No. 3,597,054 and U.S. Patent Application Publication 2011/0116076, but these references deal with detection of Ultraviolet radiation, and thus do not provide solutions for warning users of ionizing radiation.

There remains room for improvement in the area of ionizing radiation detection and warning devices.

SUMMARY OF THE INVENTION

According to a first aspect of the invention there is provided a protective eyewear device comprising a frame for supporting the protective eyewear on a user's head in a position placing one or more transparent or translucent viewing lenses of the eyewear device in front of the user's eyes, and one or more deposits of a radiation-reactive material located at or adjacent the one or more lenses and responsive to ionizing radiation exposure to produce a visual indication of said exposure to the user within a normally used field of vision of said user.

According to a second aspect of the invention there is provided an eye protection and radiation warning device comprising one or more transparent or translucent viewing lenses to be worn in front one or both eyes of a user, and one or more deposits of a radiation-reactive material that is carried with the one or more lenses and is responsive to ionizing radiation exposure to produce a visual indication of said exposure to the user at a position within a normally used field of vision of said user when the one or more viewing lenses are worn.

Preferably the reactive material is embedded within the one or more lenses.

Preferably the one or more lenses comprise polycarbonate.

Preferably the one or more deposits comprise a phosphor that luminesces under exposure to ionizing radiation.

The one or more deposits may comprise cadmium tungstate, or calcium tungstate.

According to a third aspect of the invention there is provided a method of producing an eye protection device that provides a wearer with visual warning signals in response to ionizing radiation exposure, the method comprising providing the eyewear with at least one deposit of radiation-reactive material that is carried on the eye protection device at or adjacent one or more transparent or translucent viewing lenses thereof and is responsive to said ionizing radiation exposure in a manner producing a visual indication of said exposure within a normally used field of vision of the wearer when the one or more lenses are worn in front of a user's eyes.

Preferably the method comprises impregnating at least one of the one or more viewing lenses with the radiation-reactive material.

BRIEF DESCRIPTION OF THE DRAWINGS

In the accompanying drawings, which illustrate exemplary embodiments of the present invention:

FIGS. 2A, 2B and 2C illustrate applicability of the present invention to various styles of eyewear protection, where the lenses are equipped with luminescent material to provide visual indicators of the presence of ionization radiation when the luminescence of the material is activated by the same.

DETAILED DESCRIPTION

Figure 1:
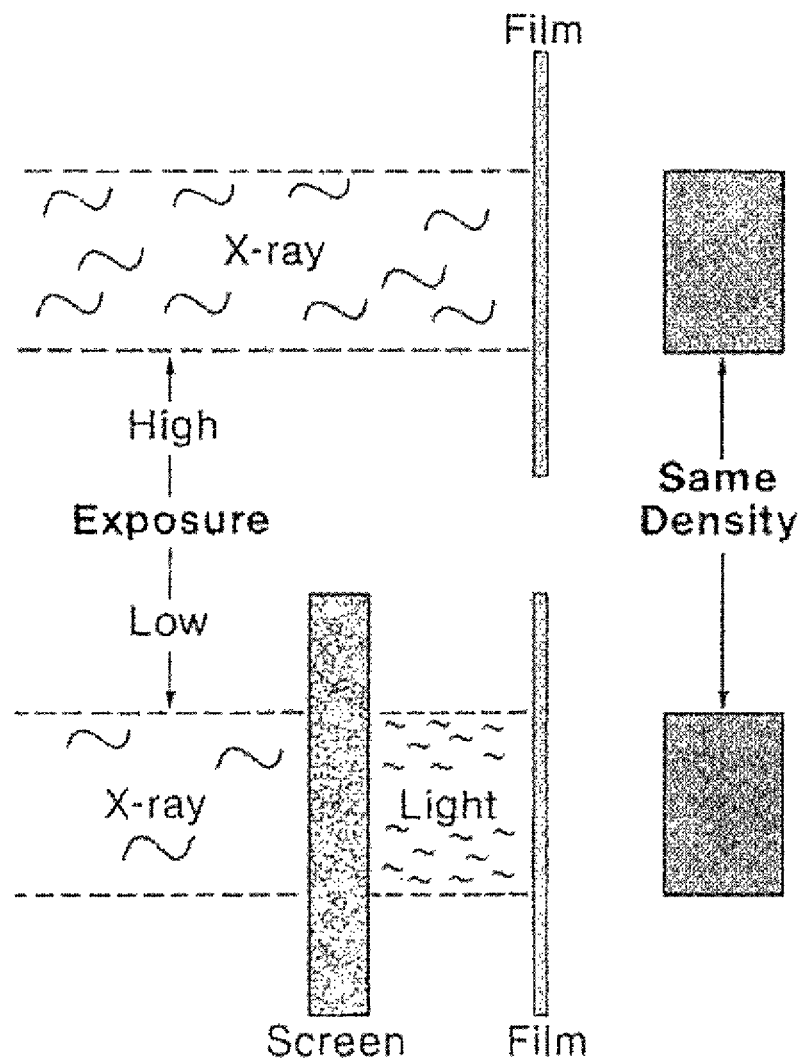
FIG. 1 is a schematic illustration demonstrating fluorescence in the context of an x-ray imaging process.

Fluorescence is the property of a material that enables it to absorb radiation energy in one portion of the photon-energy spectrum and emit some of the energy in the form of lower energy photons. Materials that glow, or emit visible light, when exposed to high-photon energy ultraviolet light have this property. FIG. 1 illustrates what happens to the x-ray energy that is absorbed by an intensifying screen in an x-ray based imaging process. In the intensifying screen, the fluorescent process creates visible light when such material is exposed to high-energy x-ray photons. The intensifying screen is an energy converter; it converts approximately 5 to 20% of the absorbed x-ray energy into light. This percentage is the conversion efficiency of the screen, and depends on the type of material used in the screen.

The present invention employs such fluorescence in order to provide visible radiation warnings to those working in environments where there is a risk of exposure to hazardous levels of ionizing radiation. In many such environments, eye protection is typically prescribed to avoid potential harmful particulate, liquid or other contaminants from reaching the eyes of the worker. Accordingly, to provide a visible warning of high radiation levels to the worker, the invention incorporates the user of phosphor materials at or adjacent the viewing lenses of the eye protection in order to place the visible warning within the wearer's normal field of vision when triggered, thereby ensuring the warning will be seen on the basis that the eye protection is mandatory or highly recommended.

Some embodiments of the present invention employ a Calcium Tungstate infused safety glass lens that give offs visible fight when in the presence of ionizing radiation, with the intention being to concentrate the calcium tungstate such that the light becomes visible at a predetermined radiation dose rate. The Canadian Nuclear Substances and Radiation Devices Regulations prescribe that radiation doses received by persons other than nuclear energy workers as a result of use or possession of an exposure device be limited to 0.1 millisievert (mSv) per week and 0.5 mSv per year, and that persons or barriers be placed to prevent entry to areas where the dose rate is greater than 0.1 mSv per hour. Accordingly, the safety glass lens should illuminate at a dose rate that is no greater, and preferably less than, the prescribed hourly exposure limit. Preferred embodiments thus activate at dose rates of less than 0.1 mSv, equivalent to 10 millirem (mrem), for example at 2.5 mrem in one embodiment. More sensitive embodiments configured to have lower threshold levels at which the luminescence is triggered may be employed, for example for other applications in which workers face the risk of unsafe levels of radiation exposure, one example of which is the mining industry.

Some embodiments include safety glasses having a small semi-circular impregnation of the active ingredient (i.e. the phosphor) at the bottom of the lens(es). However, it will be appreciated that the shape, size and location of the impregnated area may be varied. However, the center of the lens may ber left unimpregnated so that the light emitted by the phosphor when activated by sufficient radiation levels is not directly at the center of the user's field of view through the lens, where such illumination of the lens may interfere with the wearer's natural sight line. In other words, the phosphor may be isolated from the center of the lens, and located somewhere nearer the periphery thereof, at a location within the wearer's overall field of vision, but not impeding the persons ability to view through the lens.

Materials

The two major characteristics the radiation-reactive material must have are (1) high x-ray absorption and (2) fluorescence. Because of their fluorescence, the materials are often referred to as phosphors.

Soon after the discovery of x-rays, calcium tungstate became the principal material in fluorescent screens and continued to be until the 1970s. At that time, a variety of new phosphor materials were developed; many contain one of the rare earth chemical elements. Phosphor compounds now used as intensifying screen materials include: barium lead sulfate, barium strontium sulfate, barium fluorochloride, yttrium oxysulfide, lanthanum oxybromide, lanthanum oxysulfide, and gadolinium oxysulfide.

Each compound contains one element that is the primary x-ray absorber.

The probability of x-ray absorption is higher when the photon energy is just slightly higher than the K energy of the absorbing element (i.e. the binding energy of an electron in the K-shell of the absorbing element). The K-edge energy is, in turn, determined by the atomic number of the absorbing element.

Calcium tungstate, the most common screen material for many years, uses tungsten as the absorbing element. The K edge of tungsten is at 69.4 keV. For most x-ray examinations, a major portion of the x-ray beam spectrum falls below this energy. For this reason, screens containing tungsten are limited with respect to x-ray absorption. Today, most intensifying screens contain either barium, lanthanum, gadolinium, or yttrium as the absorbing element. The K edge of these elements is below a major portion of the typical x-ray beam spectrum. This increases the chance of x-ray interaction and absorption.

Spectral Characteristics

The other elements in the compound contribute to the fluorescent properties of the material. Each compound produces light of a color (wavelength) that is specific to the particular material. The light from intensifying screens is produced in either the ultraviolet, blue or green portion of the light spectrum, and intensifying screens are sometimes classified as either blue or green emitters. The significance of this is that a screen must be used with a film that has adequate sensitivity to the color of light the screen emits. Some radiographic films are sensitive only to blue light; others (orthochromatic) are also sensitive to green light. If screen and film spectral characteristics are not properly matched, receptor sensitivity is severely reduced.

Cadmium tungstate ($CdWO_4$ or CWO), the cadmium salt of tungstic acid, is a dense, chemically inert solid which is used as a scintillation crystal to detect gamma rays. It has density of 7.9 $g/cm^3$ and melting point of 1325 C. It is toxic if inhaled or swallowed. Its crystals are transparent, colorless, with slight yellow tint. It is odorless. The crystal is transparent and emits light when it is hit by gamma rays and x-rays, making it useful as a detector of ionizing radiation. Its peak scintillation wavelength is 480 nm (with emission range between 380-660 nm) and has an efficiency of 13000 photons/MeV. It has a relatively high light yield, its light output is about 40% of that of sodium iodide activated with thallium (NaI(Tl)), but the time of scintillation is quite long (12-15 μs). Combining the scintillator crystal with externally applied piece of boron carbide allows construction of compact detectors of gamma rays and neutron radiation. The typical Radio-isotope used in industrial Radiography, one of our target markets is Iridium 192. Radioactive Ir-192 decays via negative β emission and via electron capture, which results in emission of a number of gamma rays in the energy range of 0.136 MeV to 1.06 MeV. Average β energy is about 0.2 MeV whereas average gamma energy is 0.37 MeV. Very high radiopurity allows use of this scintillator as a detector of rare nuclear processes (double beta decay, other rare alpha and beta decays) in low-background applications. This would be suitable for detection in the mining sector because very low dose rates will be present from naturally occurring radiation.

Accordingly, Cadmium tungstate is an ideal crystal for some embodiments of the present invention, although the fact that it is toxic may be a challenge for regulatory approval due to potential issues concerning production as well as disposal. Accordingly, other embodiments may employ other radiation-sensitive materials that similarly react in a luminescent manner under exposure to ionizing radiation at levels which would warrant a visual warning to the user.

The present invention may be applied to any number of different eye protection devices, including various style of protective eyewear. FIG. 2 shows a number of different commercially available protective eyewear styles, each of which may be equipped with the radiation warning solution of the present invention.

FIG. 2A shows safety goggles having a single viewing lens that is held in front of both eyes with a shroud-like shield spanning the full circumference of the lens to project rearward therefrom to abut against the wearer's face around the eyes under the resilient action of an elastic headband having its opposite ends secured to the sides of the shield.

FIG. 2C shows another common single-lens protective eyewear design, where a single viewing lens again spans over both eyes of the wearer and side shields extend back from both sides of the lens to close off access to the eye area from lateral directions, but the lens and shields are supported by a frame having a pair of temples for wearing over the ears of the user to support the lens over the wearer's eyes by way of a cross member structure spanning between the forward ends of the temples.

FIG. 2B shows yet another common style of safety glasses, whose frame features a pair of foldable temples interconnected by a structure including two lens supports and a bridge therebetween, whereby two separate lenses are respectively carried by the supports to each overlie a respective one of the wearer's eyes, and the bridge joins the two lens supports together and rests on the bridge of the wearer's nose.

Each eye protection device may employ one or more deposits of the radiation-reactive material on one or more lenses. For example, with reference to FIG. 2C, a single lens device may feature two deposits D, each positioned laterally outward from the center of the single viewing lens so that each deposit lies in the field of vision of a respective one of the eyes more in line with a respective eye of the wearer (i.e. more centralized across that single eye's field of vision). Alternatively, with reference to FIG. 2A, if enough light is cast by the luminescence of the reactive material, a single deposit D' at a relatively central location across the lens may be sufficient to be detectable by each eye of the user. Positioning of one or more deposits such that the luminescent material is detectable by each eye is preferable over embodiments where the luminescent material, or at least the light cast thereby, is only within one eye's field of vision.

Likewise, with reference to FIG. 2B, a two-lens eye protection device preferably has the reactive material D present at both lenses.

An eye protection device of the present invention is preferably produced by impregnation of the radiation-reactive material into the lens or lenses, which may be made of polycarbonate, a material commonly employed for commercially available protective eyewear, although other suitable lens materials may alternatively be employed. For example, researchers at the Fraunhofer Institute for Environmental, Safety and Energy Technology, Germany, have developed processes for impregnating additives into polycarbonate using supercritical carbon dioxide, which may be suitable for production of eye protection lenses of the present invention, although other impregnation processes may also prove suitable for application in the present invention.

Other methods of securing the material to one or more components of the at or adjacent the lens or lenses so as to cast light in, or into, the wearer's normal field of vision may be employed, but the impregnation process has the advantage of embedding the material into the lens itself to ensure secure and reliable retention of the material to the eyewear at one or more locations providing the highest probability of visible detection.

If the presence of the radiation-reactive material in the lens in sufficient concentration to provide a sufficiently recognizable glow or illumination to provide an effective radiation warning signal to the wearer provides some notable degradation to the effective transparency of the lens, and particularly if this degradation is present even when the material is inactive (i.e. not luminescing), then the material is preferably embedded as a concentrated or localized deposit located away from the center of the eye's normal viewing field through the lens so as to minimize disruption to the wearer's sight line. On the other hand, if the presence of the material has little or no visible effect on viewability through the lens when inactive, the material may be distributed throughout the full area of the lens.

It will be appreciated that the term lens is being used to denote a piece of transparent or translucent material forming a window through which the eyes can view their surroundings from behind the protection of the physical barrier provided by that piece of material, regardless of whether the piece of material is suitably contoured to focus rays of light for vision correction or other purposes. That is, while the present invention may be employed for prescription eyewear providing such light focusing functionality for vision correction, the term lens is being used in its broader sense commonly understood in the field of eye protection.

It will also be appreciated that the present invention is not limited specifically to eyewear, but other headwear or headgear that likewise incorporates a lens that protects the eye while retaining at least some field of vision. In other words, the invention is not limited to devices whose functionality is dedicated entirely to the eyes (eye protection, vision correct, or a combination thereof). For example, the present invention may be employed in full face masks that substantially cover the wearer's entire face while using a transparent or translucent viewing lens or window to form all or part of this coverage.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A protective eyewear device comprising a frame for supporting the protective eyewear on a user's head in a position placing one or more transparent or translucent viewing lenses of the eyewear device in front of the user's eyes, and one or more deposits of a phosphor material that is impregnated within a lens material of the one or more lenses and is and responsive to x-ray and/or gamma-ray radiation to produce a visual indication of exposure to said x-ray and/or gamma-ray radiation to the user within a normally used field of vision of said user.

2. An eye protection and radiation warning device comprising one or more transparent or translucent viewing lenses to be worn in front one or both eyes of a user, and one or more deposits of a phosphor material that is impregnated within a lens material of the one or more lenses and is responsive to x-ray and/or gamma-ray radiation to produce a visual indication of exposure to said x-ray and/or gamma-ray radiation the user at a position within a normally used field of vision of said user when the one or more viewing lenses are worn.

3. The device of claim 1 wherein the lens material comprises polycarbonate.

4. The device of claim 1 wherein the phosphor material comprises cadmium tungstate.

5. The protective eyewear of claim 1 wherein the phosphor material comprises calcium tungstate.

6. A method of producing an eye protection device that provides a wearer with visual warning signals in response to x-ray and/or gamma-ray radiation, the method comprising impregnating a lens material of the eyewear with at least one deposit of a phosphor material that is responsive to said x-ray and/or gamma-ray radiation in a manner producing a visual indication of exposure to said x-ray and/or gamma-ray radiation within a normally used field of vision of the wearer when the one or more lenses are worn in front of a user's eyes.

7. The method of claim 6 wherein the lens material comprises polycarbonate.

8. The method of claim 6 wherein the phosphor material comprises cadmium tungstate.

9. The method of claim 6 wherein the phosphor material comprises calcium tungstate.

* * * * *